(12) United States Patent
Tsay et al.

(10) Patent No.: US 11,846,580 B2
(45) Date of Patent: Dec. 19, 2023

(54) FLOW CELL PACKAGE AND METHOD FOR MAKING THE SAME

(71) Applicants: ILLUMINA, INC., San Diego, CA (US); ILLUMINA CAMBRIDGE LIMITED, Cambridge (GB)

(72) Inventors: James Tsay, San Diego, CA (US); Anmiv Prabhu, San Diego, CA (US); David Heiner, Vista, CA (US); Edwin Li, Los Angeles, CA (US); Alexandre Richez, Cambridge (GB); John M. Beierle, Carlsbad, CA (US); Kevan Samiee, San Diego, CA (US); Kristina Munoz, Coronado, CA (US); Leonid Malevanchik, San Diego, CA (US); Ludovic Vincent, San Diego, CA (US); Naiqian Zhan, San Diego, CA (US); Peyton Shieh, San Diego, CA (US); Robert Yang, San Diego, CA (US); Samantha Schmitt, San Diego, CA (US); Sang Park, San Diego, CA (US); Scott Bailey, San Diego, CA (US); Sean M. Ramirez, San Diego, CA (US); Sunmin Ahn, San Diego, CA (US); Valerie Uzzell, Solana Beach, CA (US); Wei Wei, San Diego, CA (US); Yuxiang Huang, San Diego, CA (US); Tyler Jamison Dill, San Diego, CA (US)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 314 days.

(21) Appl. No.: 17/191,612

(22) Filed: Mar. 3, 2021

(65) Prior Publication Data
US 2021/0208055 A1   Jul. 8, 2021

Related U.S. Application Data

(63) Continuation of application No. 15/848,450, filed on Dec. 20, 2017, now Pat. No. 10,955,332.
(Continued)

(51) Int. Cl.
*G01N 15/14* (2006.01)
*C12Q 1/6874* (2018.01)
(Continued)

(52) U.S. Cl.
CPC ...... *G01N 15/1436* (2013.01); *B01J 19/0046* (2013.01); *B01L 3/502* (2013.01);
(Continued)

(58) Field of Classification Search
CPC .......... G01N 15/1436; G01N 15/1484; G01N 2015/1006; B01J 19/0046;
(Continued)

(56) References Cited

U.S. PATENT DOCUMENTS 5,861,054 A   1/1999  Miyashita et al.
6,103,479 A   8/2000  Taylor
(Continued)

FOREIGN PATENT DOCUMENTS

JP   H09194823 A    7/1997
JP   2000353866 A   12/2000
(Continued)

OTHER PUBLICATIONS

PCT/US2017/067645, "International Search Report and Written Opinion", dated Apr. 16, 2018, 18 pages.

*Primary Examiner* — Jill A Warden
*Assistant Examiner* — John McGuirk
(74) *Attorney, Agent, or Firm* — Dierker & Kavanaugh, P.C.

(57) ABSTRACT

A flow cell package includes first and second surface-modified patterned wafers and a spacer layer. The first surface-modified patterned wafer includes first depressions separated by first interstitial regions, a first functionalized molecule bound to a first silane or silane derivative in at least some of the first depressions, and a first primer grafted to the first functionalized molecule in the at least some of the first depressions. The second surface-modified patterned wafer includes second depressions separated by second interstitial regions, a second functionalized molecule bound to a second silane or silane derivative in at least some of the second depressions, and a second primer grafted to the second functionalized molecule in the at least some of the second
(Continued)

depressions. The spacer layer bonds at least some first interstitial regions to at least some second interstitial regions, and at least partially defines respective fluidic chambers of the flow cell package.

15 Claims, 4 Drawing Sheets

Related U.S. Application Data (60) Provisional application No. 62/438,316, filed on Dec. 22, 2016.

(51) Int. Cl.
| | | |
|---|---|---|
| *B01L 3/00* | (2006.01) | |
| *C09D 133/24* | (2006.01) | |
| *C09D 133/26* | (2006.01) | |
| *G01N 15/10* | (2006.01) | |
| *B01J 19/00* | (2006.01) | |

(52) U.S. Cl.
CPC ...... *B01L 3/502707* (2013.01); *C09D 133/24* (2013.01); *C09D 133/26* (2013.01); *C12Q 1/6874* (2013.01); *G01N 15/1484* (2013.01); *B01J 2219/00286* (2013.01); *B01J 2219/00317* (2013.01); *B01J 2219/00319* (2013.01); *B01J 2219/00418* (2013.01); *B01J 2219/00585* (2013.01); *B01J 2219/00596* (2013.01); *B01J 2219/00612* (2013.01); *B01J 2219/00637* (2013.01); *B01J 2219/00722* (2013.01); *B01L 2200/12* (2013.01); *B01L 2300/087* (2013.01); *B01L 2300/0829* (2013.01); *B01L 2300/0848* (2013.01); *B01L 2300/0887* (2013.01); *B01L 2300/16* (2013.01); *G01N 2015/1006* (2013.01)

(58) Field of Classification Search
CPC .... B01J 2219/00286; B01J 2219/00317; B01J 2219/00319; B01J 2219/00418; B01J 2219/00585; B01J 2219/00596; B01J 2219/00612; B01J 2219/00637; B01J 2219/00722; B01J 2219/00662; B01L 3/502; B01L 3/502707; B01L 2200/12; B01L 2300/0829; B01L 2300/0848; B01L 2300/087; B01L 2300/0887; B01L 2300/16; C09D 133/24; C09D 133/26; C12Q 1/6874; C12Q 1/68; H01L 21/3213; H01L 21/31051; H01L 21/56; C07C 247/12; B32B 3/26

See application file for complete search history.

(56) References Cited

U.S. PATENT DOCUMENTS

| | | |
|---|---|---|
| 6,130,098 A | 10/2000 | Handique et al. |
| 6,221,118 B1 | 4/2001 | Yoshida et al. |
| 6,274,351 B1 | 8/2001 | Peponnet |
| 6,347,584 B1 | 2/2002 | Kawamoto et al. |
| 8,266,791 B2 | 9/2012 | Borenstein et al. |
| 8,778,848 B2 | 7/2014 | Lin et al. |
| 8,778,849 B2 | 7/2014 | Bowen et al. |
| 8,951,716 B2 | 2/2015 | Liu et al. |
| 9,012,022 B2 | 4/2015 | George et al. |
| 9,079,148 B2 | 7/2015 | Rigatti et al. |
| 9,403,141 B2 | 8/2016 | Banyai et al. |
| 10,384,189 B2 | 8/2019 | Peck et al. |
| 2004/0226918 A1 | 11/2004 | Lee et al. |
| 2005/0089993 A1 | 4/2005 | Boccazzi et al. |
| 2008/0108512 A1 | 5/2008 | Ellinger et al. |
| 2009/0079976 A1 | 3/2009 | Cunningham et al. |
| 2010/0298171 A1* | 11/2010 | Shirazi ............... B01J 19/0046 506/40 |
| 2011/0059865 A1 | 3/2011 | Smith et al. |
| 2012/0129704 A1 | 5/2012 | Gunderson et al. |
| 2012/0270400 A1 | 10/2012 | Takegoshi et al. |
| 2013/0203324 A1 | 8/2013 | Hasegawa et al. |
| 2014/0079923 A1 | 3/2014 | George et al. |
| 2014/0243224 A1 | 8/2014 | Barnard et al. |
| 2014/0272719 A1 | 9/2014 | Liu et al. |
| 2015/0005447 A1 | 1/2015 | Berti et al. |
| 2015/0093303 A1 | 4/2015 | Tsai et al. |
| 2015/0139857 A1 | 5/2015 | Liu et al. |
| 2015/0265994 A1 | 9/2015 | Hyde et al. |
| 2016/0023208 A1 | 1/2016 | Fisher et al. |
| 2016/0122816 A1 | 5/2016 | Brown et al. |
| 2016/0246170 A1 | 8/2016 | Bowen et al. |
| 2016/0272846 A1 | 9/2016 | Tsuchiya et al. |
| 2016/0339428 A1 | 11/2016 | Jungkyu et al. |
| 2017/0151546 A1 | 6/2017 | Peck et al. |
| 2018/0037767 A1 | 2/2018 | Zhang et al. |
| 2018/0195999 A1 | 7/2018 | Liu et al. |
| 2020/0129974 A1 | 4/2020 | Ren et al. |

FOREIGN PATENT DOCUMENTS

| | | | | |
|---|---|---|---|---|
| JP | 2009182344 A | 8/2009 | | |
| JP | 2010514222 A | 4/2010 | | |
| JP | 2012109287 A | 6/2012 | | |
| WO | 2000/031148 A2 | 6/2000 | | |
| WO | 2001/001143 A2 | 1/2001 | | |
| WO | 2003/014392 A2 | 2/2003 | | |
| WO | 2008079651 A1 | 7/2008 | | |
| WO | WO-2014142841 A1 * | 9/2014 | ........ | B01L 3/502707 |
| WO | 2015005433 A1 | 1/2015 | | |
| WO | 2015015913 A1 | 2/2015 | | |
| WO | 2016/022266 A1 | 2/2016 | | |

* cited by examiner

FIG. 1

FIG. 2A  ↓ SILANIZATION

FIG. 2B  ↓ FML FORMATION

FIG. 2C ↓ POLISHING

FIG. 2D ↓ GRAFTING

FLOW CELL PACKAGE AND METHOD FOR MAKING THE SAME

CROSS-REFERENCE TO RELATED APPLICATIONS

This application is a continuation of U.S. Ser. No. 15/848,450, filed Dec. 20, 2017, which itself claims the benefit of U.S. Provisional Application Ser. No. 62/438,316, filed Dec. 22, 2016, the contents of each of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes in humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

SUMMARY

In an example of a method disclosed herein, a surface-modified patterned wafer is formed and two of the surface-modified patterned wafers are bonded together with a spacer layer therebetween. To form the surface-modified patterned wafers, a silane or a silane derivative is attached to a surface of a patterned wafer including depressions separated by interstitial regions to form silanized depressions and silanized interstitial regions. A coating layer of a functionalized molecule is formed in the silanized depressions and on the silanized interstitial regions. The coating layer is polished from the silanized interstitial regions. In some examples, the coating layer is polished from the silanized interstitial regions using i) a basic, aqueous slurry having a pH ranging from about 7.5 to about 11 and including an abrasive particle having a hardness that is less than a hardness of the patterned wafer or ii) a polishing pad and a solution free of the abrasive particle. A primer is grafted to the coating layer in the silanized depressions to form functionalized depressions.

In another example of the method disclosed herein, the method comprises forming a surface-modified patterned wafer by: plasma ashing a surface of a patterned wafer including depressions separated by interstitial regions; forming a coating layer of a functionalized molecule in the depressions and on the interstitial regions; polishing the coating layer from the interstitial regions (optionally using i) a basic, aqueous slurry having a pH having a pH ranging from about 7.5 to about 11 and including an abrasive particle having a hardness that is less than a hardness of the patterned wafer or ii) a polishing pad and a solution free of the abrasive particle); and grafting a primer to the coating layer in the depressions to form functionalized depressions. This method also comprises bonding two of the surface-modified patterned wafers together with a spacer layer therebetween.

An example of a flow cell package includes first and second surface-modified patterned wafers and a spacer layer. The first surface-modified patterned wafer includes first depressions separated by first interstitial regions, a first functionalized molecule bound to a first silane or silane derivative in at least some of the first depressions, and a first primer grafted to the first functionalized molecule in the at least some of the first depressions. The second surface-modified patterned wafer includes second depressions separated by second interstitial regions, a second functionalized molecule bound to a second silane or silane derivative in at least some of the second depressions, and a second primer grafted to the second functionalized molecule in the at least some of the second depressions. The spacer layer bonds at least some first interstitial regions to at least some second interstitial regions, and the spacer layer at least partially defines respective fluidic chambers of the flow cell package.

Another example of a flow cell package includes first and second surface-modified patterned wafers and a spacer layer, where the first surface-modified patterned wafer includes first depressions separated by first interstitial regions, a first functionalized molecule bound to the first surface-modified patterned wafer in at least some of the first depressions, and a first primer grafted to the first functionalized molecule in the at least some of the first depressions. The second surface-modified patterned wafer includes second depressions separated by second interstitial regions, a second functionalized molecule bound to the second surface-modified patterned wafer in at least some of the second depressions, and a second primer grafted to the second functionalized molecule in the at least some of the second depressions. The spacer layer bonds at least some first interstitial regions to at least some second interstitial regions, and the spacer layer at least partially defines respective fluidic chambers of the flow cell package.

In an example of a method for using the flow cell package, the flow cell package is diced into individual flow cells containing at least two of the respective fluidic chambers. In another example of a method for using the flow cell package, the flow cell package is diced into individual flow cells containing at least one of the respective fluidic chambers.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 2A through 2E are cross-sectional views which together illustrate an example of a method for forming a surface-modified patterned wafer;

INTRODUCTION

In an aspect, a method comprises forming a surface-modified patterned wafer by: attaching a silane or a silane derivative to a surface of a patterned wafer including depressions separated by interstitial regions, thereby forming silanized depressions and silanized interstitial regions; forming a coating layer of a functionalized molecule in the silanized depressions and on the silanized interstitial regions; polishing the coating layer from the silanized interstitial regions (optionally using i) a basic, aqueous slurry having a pH ranging from about 7.5 to about 11 and including an abrasive particle having a hardness that is less than a hardness of the patterned wafer or ii) a polishing pad and a solution free of the abrasive particle); and grafting a primer to the coating layer in the silanized depressions to form functionalized depressions. The method also comprises bonding two of the surface-modified patterned wafers together with a spacer layer therebetween.

In one example of this aspect, attaching the silane or the silane derivative to the surface of the patterned wafer involves at least one of vapor deposition and Yield Engineering Systems (YES) method. In another example, the attaching involves chemical vapor deposition (CVD). In other examples, the attaching involves plasma-enhanced CVD, initiated CVD, metal-organic CVD, or other deposition methods.

In one example of this aspect, forming the coating layer of the functionalized molecule involves reacting a functional group of the functionalized molecule with an unsaturated moiety of the silane or silane derivative, and wherein the unsaturated moiety is selected from the group consisting of cycloalkenes, cycloalkynes, heterocycloalkenes, heterocycloalkynes, substituted variants thereof, and combinations thereof.

In another example of this aspect, forming the coating layer of the functionalized molecule includes depositing a solution including the functionalized molecule onto the silanized depressions and the silanized interstitial regions, and curing the functionalized molecule. In some examples, the curing serves to form covalent bonds between the functionalized molecule and the silane or silane derivative.

In another example of this aspect, forming the coating layer of the functionalized molecule includes depositing a solution including the functionalized molecule onto the depressions and interstitial regions of the surface-modified patterned wafer and curing the functionalized molecule. In such examples, the functionalized molecule may form covalent bonds with the wafer surface. In some examples, the wafer surface is treated to plasma ashing conditions prior to deposition of the functionalized molecule on the wafer surface.

In one example aspect of the method, the basic, aqueous slurry including further includes a chelating agent, a surfactant, a dispersant, or combinations thereof.

In one example of this aspect, grafting of the primer to the coating layer involves dunk coating, spray coating, puddle dispensing, or combinations thereof.

In one example of this aspect, the method further comprises plasma ashing the patterned wafer prior to attaching the silane or the silane derivative.

In this aspect of the method, the coating layer of the functionalized molecule has a thickness of about 200 nm or less.

This aspect of the method can further comprise dicing the bonded surface-modified patterned wafers into respective flow cells.

In examples of this aspect of the method, the spacer layer comprises a radiation-absorbing material. In these examples, bonding involves positioning the radiation-absorbing material at an interface between the two surface-modified patterned wafers such that the radiation-absorbing material contacts at least some of the interstitial regions of each of the two surface-modified patterned wafers and applying compression at the interface and irradiating the radiation-absorbing material. In other examples of this aspect of the method, the spacer layer includes a radiation-absorbing material in contact therewith. In these examples, bonding involves positioning the radiation-absorbing material at a respective interface between the spacer layer and each of the two surface-modified patterned wafers such that the radiation-absorbing material contacts at least some of the interstitial regions of each of the two surface-modified patterned wafers, and applying compression at the respective interfaces and irradiating the radiation-absorbing material. In some examples of these approaches, the interstitial regions in contact with the radiation-absorbing material are silanized as described herein (e.g., due to residual silane left on the surface following polishing) and/or activated by plasma ashing.

In an example of this aspect of the method, the abrasive particle is selected from the group consisting of calcium carbonate, agarose, and graphite. In other examples, the abrasive particle is silica, aluminum oxide, or cerium oxide. In some examples, the abrasive particle is silica.

It is to be understood that any features of this aspect of the method may be combined together in any desirable manner and/or configuration.

In another aspect, the method comprises forming a surface-modified patterned wafer by: plasma ashing a surface of a patterned wafer including depressions separated by interstitial regions; forming a coating layer of a functionalized molecule in the depressions and on the interstitial regions; polishing the coating layer from the interstitial regions (optionally using i) a basic, aqueous slurry having a pH ranging from about 7.5 to about 11 and including an abrasive particle having a hardness that is less than a hardness of the patterned wafer or ii) a polishing pad and a solution free of the abrasive particle); and grafting a primer to the coating layer in the depressions to form functionalized depressions. The method also comprises bonding two of the surface-modified patterned wafers together with a spacer layer therebetween.

In an example of this other aspect of the method, the abrasive particle is selected from the group consisting of calcium carbonate, agarose, and graphite. In other examples, the abrasive particle is silica, aluminum oxide, or cerium oxide.

It is to be understood that any features of this aspect of the method may be combined together in any desirable manner. Moreover, it is to be understood that any combination of features of this aspect of the method and/or of the first aspect of the method may be used together, and/or that any features from either or both of these aspects may be combined with any of the examples disclosed herein.

In some examples of the several methods, the two surface-modified patterned wafers are positioned so that at least some of the functionalized depressions of one of the two surface-modified patterned wafers are aligned with a respective functionalized depression of another of the two surface-modified patterned wafers to form a fluidic chamber, and the spacer layer defines longitudinal walls between adjacent fluidic chambers. In some aspects, the two surface-modified patterned wafers are positioned so that at least some of the functionalized depressions of one of the two surface-modified patterned wafers are aligned with respective functionalized depressions of the other of the two surface-modified patterned wafers to form aligned functionalized depression pairs, wherein the two surface-modified patterned wafers define the top and bottom of a plurality of fluidic chambers and the spacer layer defines longitudinal walls between adjacent fluidic chambers, and wherein each fluidic chamber comprises a plurality of aligned functionalized depression pairs.

In some examples of the several methods, each of the functionalized depressions is in a flow channel defined by the two bonded surface-modified patterned wafers. In some examples, each functionalized depression is one of a plurality of wells within the flow channel.

An aspect of a flow cell package comprises a first surface-modified patterned wafer, which includes first depressions separated by first interstitial regions, a first functionalized molecule bound to a first silane or a first silane derivative in at least some of the first depressions, and a first primer grafted to the first functionalized molecule in the at least some of the first depressions; a second surface-modified patterned wafer, which includes second depressions separated by second interstitial regions, a second functionalized molecule bound to a second silane or a second silane derivative in at least some of the second depressions, and a second primer grafted to the second functionalized molecule in the at least some of the second depressions; and a spacer layer bonding at least some of the first interstitial regions to at least some of the second interstitial regions, wherein the spacer layer at least partially defines respective fluidic chambers of the flow cell package.

In an example of this aspect of the flow cell package, the at least some of the first depressions and the at least some of the second depressions are aligned to form one of the respective fluidic chambers, and the spacer layer forms longitudinal walls between adjacent fluidic chambers. In this example, at least one of the first and second depressions is: in a flow channel defined by the two bonded surface-modified patterned wafers; or is one of a plurality of wells within the flow channel. In some aspects, the two surface-modified patterned wafers are positioned so that at least some of the functionalized depressions of one of the two surface-modified patterned wafers are aligned with respective functionalized depressions of the other of the two surface-modified patterned wafers to form aligned functionalized depression pairs, wherein the two surface-modified patterned wafers define the top and bottom of a plurality of fluidic chambers and the spacer layer defines longitudinal walls between adjacent fluidic chambers, and wherein each fluidic chamber comprises a plurality of aligned functionalized depression pairs.

In an example of this aspect of the flow cell package, each of the first functionalized molecule and the second functionalized molecule includes a recurring unit of Formula (I):

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the $-(CH_2)_p-$ can be optionally substituted;
p is an integer in the range of 1 to 50;
n is an integer in the range of 1 to 50,000; and
m is an integer in the range of 1 to 100,000.

One of ordinary skill in the art will recognize that a polymer comprising recurring units of Formula (I) encompasses a plurality of "n" and "m" subunits present in random order throughout the polymer. One of ordinary skill will also recognize that other monomeric components may be present in the polymer.

In another aspect, each of the first functionalized molecule and the second functionalized molecule comprises a recurring unit of Formula (Ia):

wherein:
R¹ is H or alkyl;
R⁴ is selected from the group consisting of amino, optionally substituted alkenyl, optionally substituted alkynyl, oxo-amino, azido, formyl, halo, hydroxyl, hydrazinyl, hydrazonyl, triazinyl, carboxy, glcyidyl, activated ester, aziridinyl, triazolinyl, epoxy, and thiol; each of the —(CH₂)$_o$— groups is optionally substituted; and
o is an integer between 1 and 50.

In some examples, the first and second functionalized molecules are covalently bound to the first silane or silane derivative, or to the second silane or silane derivative, respectively.

In this example, the first functionalized molecule is covalently bound to the first silane or the first silane derivative through a first unsaturated moiety of the first silane or first silane derivative; the second functionalized molecule is covalently bound to the second silane or the second silane derivative through a second unsaturated moiety of the second silane or second silane derivative; and the unsaturated moieties are individually selected from the group consisting of norbornene, heteronorbornenes, norbornene derivatives, transcyclooctene, transcyclooctene derivatives, cyclooctyne, bicycloalkynes, optionally substituted variants thereof, and combinations thereof.

In an example of this aspect of the flow cell package, the spacer layer is a black polyimide. Further examples of suitable spacer layer materials are polyester films, polyethylene films, cyclo olefin polymers (e.g., Zeonor®), acrylonitrile butadiene styrene (ABS), polycarbonate (PC) films, and the like.

In an example of this aspect of the flow cell package, each of the first surface-modified patterned wafer and the second surface-modified patterned wafer has a diameter ranging from about 200 mm to about 300 mm. In an example, the patterned wafers are circular, oval, or rectangular in shape. In other examples, the patterned wafers are circular, and have a diameter ranging from about 200 mm to about 300 mm.

It is to be understood that any features of this aspect of the flow cell package may be combined together in any desirable manner. Moreover, it is to be understood that any combination of features of this aspect of the flow cell package and/or of the method may be used together, and/or that any features from either or both of these aspects may be combined with any of the examples disclosed herein.

An aspect of a method for using the flow cell package comprises dicing the flow cell package into individual flow cells containing at least two of the respective fluidic chambers. In another aspect, a method for using the flow cell package comprises dicing the flow cell package into individual flow cells containing at least two of the respective flow channels or fluidic chambers.

It is to be understood that any features of the method for using the flow cell package may be combined together in any desirable manner. Moreover, it is to be understood that any combination of features from either or both of the methods and/or from the flow cell package may be used together, and/or that any features from any or all of these aspects may be combined with any of the features of the examples disclosed herein.

DETAILED DESCRIPTION

Examples of the method disclosed herein involve open wafer processing to deposit surface chemistry (e.g., silanization, functionalized molecule layer, primers) on patterned wafers to form surface-modified patterned wafers. The surface-modified patterned wafers may then be incorporated into a flow cell package that can be divided into flow cells that are suitable for use in biological applications, such as sequencing.

The open wafer process disclosed herein is scalable and enables high volume assembly, including high volume coating and grafting, of the surface-modified patterned wafer prior to performing any bonding to form the flow cell package. The open wafer process also enables the reproducible, stable deposition of the surface chemistry without deleteriously affecting the underlying patterned wafer.

The open wafer process also enables a variety of metrology/analytical techniques to be used for quality control and characterization. Prior to being bonded to form the flow cell package, the surface-modified patterned wafer may be exposed to, for example, atomic force microscopy (AFM), scanning electron microscopy (SEM), ellipsometry, goniometry, scatterometry, and/or fluorescence techniques.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell package and/or the various components of the flow cell package. It is to be understood that these directional terms are not meant to imply a specific orientation, but are used to designate relative orientation between components. The use of directional terms should not be interpreted to limit the examples disclosed herein to any specific orientation(s).

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like. The alkenyl group may be designated as, for example, "C2-4 alkenyl," which indicates that there are two to four carbon atoms in the alkenyl chain.

As used herein, "alkynyl" refers to a straight or branched hydrocarbon chain containing one or more triple bonds. The alkynyl group may have 2 to 20 carbon atoms. The alkynyl group may be designated, for example, as "C2-4 alkynyl," which indicates that there are two to four carbon atoms in the alkynyl chain.

An "amino" functional group refers to an —NR$_a$R$_b$ group, where R$_a$ and R$_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, which may be designated as C6-18. Examples of aryl groups include phenyl, naphthyl, azulenyl, and anthracenyl.

As used herein, the term "attached" refers to the state of two things being joined, fastened, adhered, connected or bound to each other. For example, a nucleic acid can be attached to a coating layer of a functionalized molecule by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

An "azide" or "azido" functional group refers to —N$_3$.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms (i.e., C3-20). Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —C(O)OH.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkane" means a carbocyclyl ring or ring system having at least one double bond, wherein no ring in the ring system is aromatic. Examples include cyclohexenyl or cyclohexene and norbornene or norbornenyl. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, the term "coating layer of a functionalized molecule" is intended to mean a semi-rigid or non-rigid (e.g., gelatinous) material that is permeable to liquids and gases. Typically, the coating layer of the functionalized molecule is a hydrogel that can swell when liquid is taken up and can contract when liquid is removed by drying.

The term "depositing," as used herein, refers to any suitable application technique, which may be manual or automated. Generally, depositing may be performed using vapor deposition techniques, coating techniques, grafting techniques, or the like. Some specific examples include chemical vapor deposition (CVD), spray coating, spin coating, dunk or dip coating, screen printing, slot die coating, stripe coating, puddle dispensing, or the like.

As used herein, the term "depression" refers to a discrete concave feature in a patterned wafer having a surface opening that is completely surrounded by interstitial region(s) of the patterned wafer surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or a flow channel. Also as used herein, a "functionalized depression" refers to the discrete concave feature where the coating layer of the functionalized molecule and primer(s) are attached.

The term "each," when used in reference to a collection of items, is intended to identify an individual item in the collection, but does not necessarily refer to every item in the collection. Exceptions can occur if explicit disclosure or context clearly dictates otherwise.

As used herein, a "flow channel" can be a depression defined in a surface of a wafer that extends along a substantial portion of the wafer, or can be an area defined between two bonded surface-modified patterned wafers that has a plurality of depressions therein. A flow cell may comprise a plurality of flow channels. In some aspects, each flow cell comprises at least two, three, four flow channels.

A "fluidic chamber" is an area of a flow cell package that can receive a liquid sample. The fluidic chamber is defined between two bonded surface-modified patterned wafers, and a spacer layer defines longitudinal walls of the fluidic chamber.

The "functionalized molecule" referred to herein includes functional groups selected from optionally substituted alkenyl, azide/azido, optionally substituted amino, carboxyl, optionally substituted hydrazone, optionally substituted hydrazine, hydroxyl, optionally substituted tetrazole, optionally substituted tetrazine, nitrile oxide, nitrone, or thiol. In other aspects, the functionalized molecule includes functional groups selected from those listed above as well as epoxy, formyl, glycidyl, triazinyl, aziridinyl, oxo-amino, and halo groups. In some examples, the functionalized molecule is not norbornene or polymerized norbornene. In an example, the functionalized molecule comprises recurring units of Formula (I) or (Ia). In an example, the functionalized molecule is poly(N-(5-azidoacetamidylpentyl)acrylamide-co-acrylamide) (PAZAM).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). The heterocyclyl group may be designated as "3-6 membered heterocyclyl" or similar designations. In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a group in which R$_a$ and R$_b$ are previously defined herein.

As used herein, "hydroxyl" is an —OH group.

As used herein, the term "interstitial region" refers to an area in a substrate/wafer or on a surface that separates other areas of the substrate/wafer or surface. For example, an interstitial region can separate one feature of an array from another feature of the array. The two features that are separated from each other can be discrete, i.e., lacking contact with each other. In another example, an interstitial region can separate a first portion of a feature from a second portion of a feature. In many examples, the interstitial region is continuous whereas the features are discrete, for example, as is the case for a plurality of wells defined in an otherwise continuous or planar surface. The separation provided by an interstitial region can be partial or full separation. Interstitial regions may have a surface material that differs from the surface material of the features defined in the surface. For example, features of an array can have an amount or concentration of the coating layer and primer(s) that exceeds the amount or concentration present at the interstitial regions. In some examples, coating layer and primer(s) may not be present at the interstitial regions.

"Nitrile oxide," as used herein, means a "R$_a$C≡N$^+$O—" group in which R$_a$ is previously defined herein. Examples of preparing nitrile oxide include in situ generation from aldoximes by treatment with chloramide-T or through action of base on imidoyl chlorides [RC(Cl)=NOH].

"Nitrone," as used herein, means a "R$_a$R$_b$C≡NR$_c$$^+$O—" group in which R$_a$ and R$_b$ are previously defined herein and R$_c$ is selected from C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The term "open wafer processing," as used herein, refers to a series of sequential processes used to modify the surface of a patterned wafer with surface chemistry prior to any bonding process.

The term "patterned wafer" refers to a substrate (e.g., wafer) with a surface in which or on which depressions are defined. The substrate is generally rigid and is insoluble in aqueous liquid. The substrate may be inert to a chemistry that is used to modify or apply the coating layer of the functionalized molecule. For example, a substrate can be inert to chemistry used to attach the coating layer to the silane or silane derivative layer, or to the activated surface layer, and/or to chemistry used to attach the primer(s) to the coating layer in a method set forth herein. Examples of suitable substrates include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics, silica, fused silica, or silica-based materials such as silsesquioxane and/or polyhedral oligomeric silsesquioxane (POSS) materials, aluminum silicate, silicon and modified silicon, silicon nitride, tantalum oxide, carbon, metals, inorganic glasses, and optical fiber bundles. The hardness of the substrate (or patterned wafer) may range from about 5 GPa to about 6 GPa.

As used herein, "plasma ashing" refers to a process of removing organic matter from a patterned wafer by an oxygen plasma. The products that result from plasma ashing may be removed with a vacuum pump/system. Plasma ashing can activate the patterned wafer by introducing reactive hydroxyl groups (—OH groups bound to carbon or silicon) or carboxyl groups. Plasma ashing can also serve to activate the wafer by removing organic matter from a surface.

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the coating layer of the functionalized molecule. The primer length can be any number of bases long and can include a variety of non-natural nucleotides. In an example, the sequencing primer is a short strand, including from 20 to 40 bases.

As used herein, the terms "silane" and "silane derivative" refer to an organic or inorganic compound containing one or more silicon atoms. An example of an inorganic silane compound is SiH$_4$, or halogenated SiH$_4$ where hydrogen is replaced by one or more halogen atoms. An example of an organic silane compound is X—R$^B$—Si(OR$^C$)$_3$, wherein X is a nonhydrolyzable organic group, such as amino, vinyl, epoxy, methacrylate, sulfur, alkyl, alkenyl, alkynyl; R$^B$ is a spacer, for example —(CH$_2$)$_n$—, wherein n is 0 to 1000; R$^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. In some instances, each R$^C$ is the same, and in others, they may be different. In some examples, X is alkenyl or cycloalkenyl, R$^B$ is —(CH$_2$)$_n$—, wherein n is 2 to 6, and/or R$^C$ is alkyl. In another example, a silane compound is X—$R^B$—Si($R^D$)$_3$, where X and $R^B$ are as defined above, and each $R^D$ is independently $R^C$ or $OR^C$. In some examples, X comprises a substrate or support. As used herein, the terms "silane" and "silane derivative" can include mixtures of different silane and/or silane derivative compounds.

In some examples, the silane or silane derivative includes an unsaturated moiety that is capable of reacting with a functional group of the functionalized molecule. As used herein, the term "unsaturated moiety" refers to a chemical group includes cycloalkenes, cycloalkynes, heterocycloalkenes, heterocycloalkynes, or optionally substituted variants thereof including at least one double bond or one triple bond. The unsaturated moieties can be mono-valent or di-valent. When the unsaturated moiety is mono-valent, cycloalkene, cycloalkyne, heterocycloalkene, and heterocycloalkyne are used interchangeably with cycloalkenyls, cycloalkynyls, heterocycloalkenyl, and heterocycloalkynyl, respectively. When the unsaturated moiety is di-valent, cycloalkene, cycloalkyne, heterocycloalkene, and heterocycloalkyne are used interchangeably with cycloalkenylene, cycloalkynylene, heterocycloalkenylene, and heterocycloalkynylene, respectively. In some examples, the unsaturated moiety is a norbornyl or norbornyl derivative. In other examples, the unsaturated moiety is a norbornyl.

The unsaturated moiety can be covalently attached either directly to the silicon atoms of the silane or silane derivative, or indirectly attached via linkers. Examples of suitable linkers include optionally substituted alkylenes (i.e., bivalent saturated aliphatic radical (such as ethylene) regarded as derived from an alkene by opening of the double bond or from an alkane by removal of two hydrogen atoms from different carbon atoms), substituted polyethylene glycols, or the like. In some examples, the linker is an ethylene.

The "spacer layer," as used herein refers to a material that bonds two surface-modified patterned wafers together. In some examples, the spacer layer can be a radiation-absorbing material that aids in bonding, or can be put into contact with a radiation-absorbing material that aids in bonding.

The term "surface chemistry," as used herein refers in some aspects to a silane or silane derivative, a coating layer of a functionalized molecule, and primer(s) attached to at least a portion of the coating layer on a surface of a patterned wafer. In other aspects, "surface chemistry" refers to a coating layer of a functionalized molecule on the activated surface of the patterned wafer, and primer(s) attached to at least a portion of the coating layer.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

As used herein, the term "YES method" refers a chemical vapor deposition process developed by Illumina, Inc. which uses the chemical vapor deposition tool provided by Yield Engineering Systems ("YES"). The tool includes three different vapor deposition systems. The automated YES-VertaCoat silane vapor system is designed for volume production with a flexible wafer handling module that can accommodate 200 mm or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

The aspects and examples set forth herein and recited in the claims can be understood in view of the above definitions.

Examples of the surface-modified patterned wafers, the flow cell package, and methods for making and using the same will now be described in reference to the figures.

Figure 1:
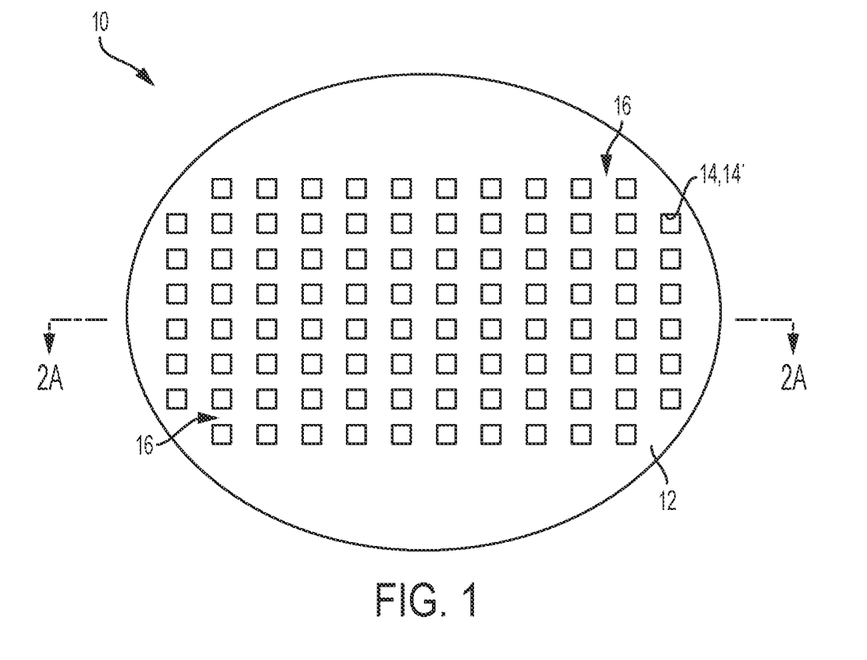
FIG. 1 is a top view of an example patterned wafer including depressions separated by interstitial regions.
Figure 2A:
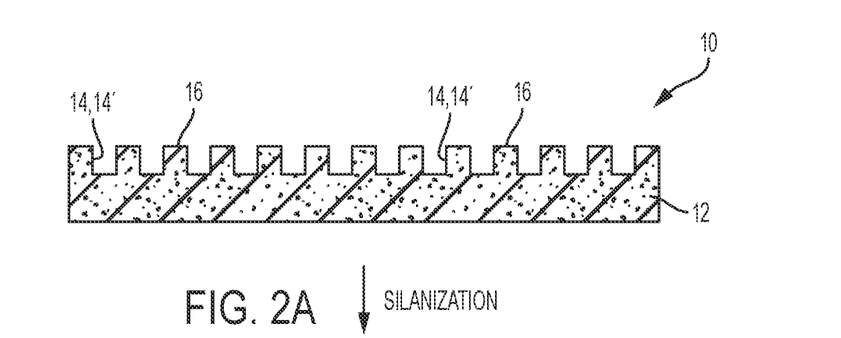
FIG. 2A is a cross-sectional view, taken along line 2A-2A, of the patterned wafer of FIG. 1.

FIG. 1 is a top view of a patterned wafer 10, and FIG. 2A is a cross-sectional view of the patterned wafer 10. The patterned wafer 10 includes a wafer/substrate 12, depressions 14 defined on or in an exposed layer or surface of the substrate 12, and interstitial regions 16 separating adjacent depressions 14. In the examples disclosed herein, the depressions 14 become functionalized with surface chemistry, while the interstitial regions 16 may be used for bonding but will not have primer(s) (shown in FIG. 2E) present thereon.

Any example of the substrate 12 previously described may be used. In an example, the substrate 12 has a diameter ranging from about 200 mm to about 300 mm.

The depressions 14 may be fabricated in or on the substrate 12 using a variety of techniques, including, for example, photolithography, nanoimprint lithography, stamping techniques, embossing techniques, molding techniques, microetching techniques, printing techniques, liftoff techniques, etc. As will be appreciated by those in the art, the technique used will depend on the composition and shape of the wafer/substrate 12 and the nature of the substrate material.

Many different layouts of the depressions 14 may be envisaged, including regular, repeating, and non-regular patterns. In an example, the depressions 14 are disposed in a hexagonal grid for close packing and improved density. Other layouts may include, for example, rectilinear (i.e., rectangular) layouts (see FIG. 4B), triangular layouts, and so forth. As shown in FIG. 1, the layout or pattern can be an x-y format of depressions 14 that are in rows and columns. In some other examples, the layout or pattern can be a repeating arrangement of depressions 14 and/or interstitial regions 16. In still other examples, the layout or pattern can be a random arrangement of depressions 14 and/or interstitial regions 16. The pattern may include spots, pads, wells, posts, stripes, swirls, lines, triangles, rectangles (e.g., defining flow channels 14" shown in FIG. 4A), circles, arcs, checks, plaids, diagonals, arrows, squares, and/or cross-hatches. Still other examples of patterned surfaces that can be used in the examples set forth herein are described in U.S. Pat. Nos. 8,778,849; 9,079,148; 8,778,848; and U.S. Patent Publication No. 2014/0243224, each of which is incorporated herein by reference in its entirety.

The layout or pattern may be characterized with respect to the density of the depressions 14 (i.e., number of depressions 14) in a defined area. For example, the depressions 14 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$, about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of depressions 14 on the substrate 12 can be between one of the lower values and one of the upper values selected from the ranges above. As examples, a high density array may be characterized as having depressions 14 separated by less than about 100 nm, a medium density array may be characterized as having depressions 14 separated by about 400 nm to about 1 μm, and a low density array may be characterized as having depressions 14 separated by greater than about 1 μm.

The layout or pattern may also or alternatively be characterized in terms of the average pitch, i.e., the spacing from the center of the one depression 14 to the center of an adjacent depression (center-to-center spacing). The pattern can be regular such that the coefficient of variation around the average pitch is small, or the pattern can be non-regular in which case the coefficient of variation can be relatively large. In either case, the average pitch can be, for example, at least about 10 nm, about 0.1 μm, about 0.5 μm, about 1 μm, about 5 μm, about 10 μm, about 100 μm, or more. Alternatively or additionally, the average pitch can be, for example, at most about 100 μm, about 10 μm, about 5 μm, about 1 μm, about 0.5 μm, about 0.1 μm, or less. The average pitch for a particular pattern of sites 16 can be between one of the lower values and one of the upper values selected from the ranges above. In an example, the depressions 14 have a pitch (center-to-center spacing) of about 1.5 μm.

In the example shown in FIGS. 1 and 2A, the depressions 14 are wells 14', and thus the substrate 12 includes an array of wells 14' in a surface thereof. The wells 14' may be micro wells or nanowells. Each well 14' may be characterized by its volume, well opening area, depth, and/or diameter.

Each well 14' can have any volume that is capable of confining a liquid. The minimum or maximum volume can be selected, for example, to accommodate the throughput (e.g. multiplexity), resolution, analyte composition, or analyte reactivity expected for downstream uses of the array 10. For example, the volume can be at least about $1 \times 10^{-3}$ μm$^3$, about $1 \times 10^{-2}$ μm$^3$, about 0.1 μm$^3$, about 1 μm$^3$, about 10 μm$^3$, about 100 μm$^3$, or more. Alternatively or additionally, the volume can be at most about $1 \times 10^4$ μm$^3$, about $1 \times 10^3$ μm$^3$, about 100 μm$^3$, about 10 μm$^3$, about 1 μm$^3$, about 0.1 μm$^3$, or less. It is to be understood that the coating layer of the functionalized molecule can fill all or part of the volume of a well 14'. The volume of the coating layer in an individual well 14' can be greater than, less than or between the values specified above.

The area occupied by each well opening on a surface can be selected based upon similar criteria as those set forth above for well volume. For example, the area for each well opening on a surface can be at least about $1 \times 10^{-3}$ μm$^2$, about $1 \times 10^{-2}$ μm$^2$, about 0.1 μm$^2$, about 1 μm$^2$, about 10 μm$^2$, about 100 μm$^2$, or more. Alternatively or additionally, the area can be at most about $1 \times 10^3$ μm$^2$, about 100 μm$^2$, about 10 μm$^2$, about 1 μm$^2$, about 0.1 μm$^2$, about $1 \times 10^{-2}$ μm$^2$, or less.

The depth of each well 14' can be at least about 0.1 μm, about 1 μm, about 10 μm, about 100 μm, or more. Alternatively or additionally, the depth can be at most about $1 \times 10^3$ μm, about 100 μm, about 10 μm, about 1 μm, about 0.1 μm, or less.

In some instances, the diameter of each well 14' can be at least about 50 nm, about 0.1 μm, about 0.5 μm, about 1 μm, about 10 μm, about 100 μm, or more. Alternatively or additionally, the diameter can be at most about $1 \times 10^3$ μm, about 100 μm, about 10 μm, about 1 μm, about 0.5 μm, about 0.1 μm, or less (e.g., about 50 nm).

The patterned wafer 10 may be exposed to a series of processes in order to modify the surface of at least the depression(s) 14. FIGS. 2B through 2E illustrate the processes to form the surface-modified patterned wafer 10' (shown in FIG. 2E).

While not shown, it is to be understood that the patterned wafer 10 may be exposed to a plasma ashing in order to clean and activate the surface. For example, the plasma ashing process may remove organic material and introduce surface hydroxyl or carboxyl groups.

The patterned wafer 10 (shown in FIG. 2A) may then be exposed to silanization, which attaches the silane or the silane derivative 18 (FIG. 2B) to the patterned wafer surface. Silanization introduces the silane or the silane derivative 18 across the surface, including in the depression 14, 14' (e.g., on the bottom surface and along the side walls) and on the interstitial regions 16.

Silanization may be accomplished using any silane or silane derivative 18. The selection of the silane or silane derivative 18 may depend, in part, upon the functionalized molecule that is to be used to form the coating layer 20 (shown in FIG. 2C), as it may be desirable to form a covalent bond between the silane or silane derivative 18 and the subsequently deposited functionalized molecule. The method used to attach the silane or silane derivative 18 to the substrate 12 may vary depending upon the silane or silane derivative 18 that is being used. Several examples are set forth herein.

In an example, the silane or silane derivative 18 is (3-aminopropyl)triethoxysilane (APTES) or 3-aminopropyl)trimethoxysilane (APTMS) (i.e., X—R$^B$—Si(OR$^C$)$_3$, wherein X is amino, R$^B$ is —(CH$_2$)$_3$—, and R$^C$ is ethyl or methyl). In this example, the substrate 12 surface may be pre-treated with the (3-aminopropyl)triethoxysilane (APTES) or 3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm$^2$ to 30 J/cm$^2$ of energy generates an active nitrene species, which can readily undergo a variety of insertion reactions with PAZAM (e.g., the functionalized molecule).

Other silanization methods may also be used. Examples of suitable silanization methods include vapor deposition, the YES method, spin coating, or other deposition methods. Some examples of methods and materials that may be used to silanize the substrate 12 in the examples of the present disclosure are described in U.S. Patent Publication No. 2015/0005447, which is incorporated herein by reference in its entirety.

In an example utilizing the YES CVD oven, the patterned wafer 10 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative 18 (e.g., liquid norbornene silane) may be deposited inside a glass vial and placed inside a glass vacuum desiccator with a patterned wafer 10. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivative 18, such as those silane or silane derivatives 18 including examples of the unsaturated moieties disclosed herein. As examples, these methods may be used when the silane or silane derivative 18 includes a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo [4.2.1]non-1(8)-ene, and bicyclo[4.2.1]non-1-ene. Any of these cycloalkenes can be substituted as described in U.S. Patent Publication No. 2015/0005447. An example of the norbornene derivative includes [(5-bicyclo[2.2.1]hept-2-enyl)ethyl]trimethoxysilane. As other examples, these methods may be used when the silane or silane derivative 18 includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo[6.1.0]non-3-yne). These cycloalkynes can be substituted as described in U.S. Patent Publication No. 2015/0005447.

Figure 2B:
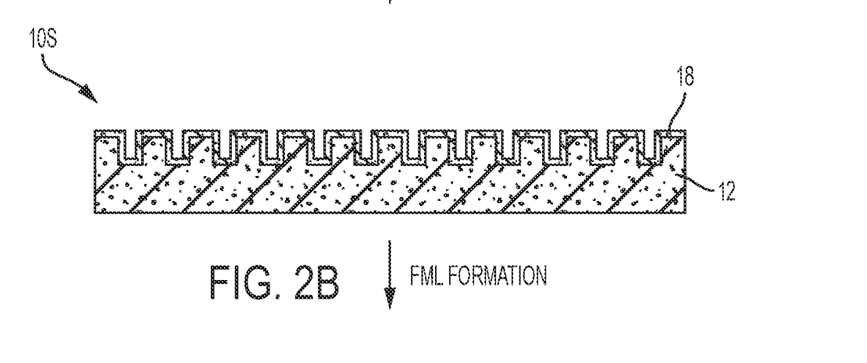

As shown in FIG. 2B, the attachment of the silane or silane derivative 18 forms a silanized patterned wafer 10S, including silanized depressions and silanized interstitial regions.

The silanized patterned wafer 10S may then be exposed to a process that will form a coating layer 20 of the functionalized molecule on the silanized depressions and silanized interstitial regions. This process is represented by the phrase "FML (functionalized molecule layer) formation" between FIGS. 2B and 2C.

Examples of the functionalized molecule include compounds comprising recurring units of Formula (I) or Formula (Ia) as defined herein.

A particular example of a functionalized molecule is poly(N-(5-azidoacetamidylpentyl)acrylamide-co-acrylamide, PAZAM (see for example, U.S. Patent Publication Nos. 2014/0079923 A1, or 2015/0005447 A1, each of which is incorporated herein by reference in its entirety), which comprises the structure shown below:

wherein n is an integer in the range of 1-20,000, and m is an integer in the range of 1-100,000. As with Formula (I), one of ordinary skill in the art will recognize that the "n" and "m" subunits are separate recurring units that are present in random order throughout the polymer structure.

The molecular weight of the functionalized molecule or PAZAM may range from about 10 kDa to about 1500 kDa, or may be, in a specific example, about 312 kDa.

In some examples, the functionalized molecule or PAZAM is a linear polymer. In some other embodiments, the functionalized molecule or PAZAM is a lightly cross-linked polymer. In some embodiments, the functionalized molecule comprises branching.

Other functionalized molecules may be used to form the coating layer 20, as long as they are functionalized to interact with the patterned wafer 12 and the subsequently applied primer(s) 22. Other examples of suitable functionalized molecules include those having a colloidal structure, such as agarose; or a polymer mesh structure, such as gelatin; or a cross-linked polymer structure, such as polyacrylamide polymers and copolymers, silane free acrylamide (SFA, see, for example, U.S. Patent Publication No. 2011/0059865, which is incorporated herein by reference in its entirety), or an azidolyzed version of SFA. Examples of suitable polyacrylamide polymers may be formed from acrylamide and an acrylic acid or an acrylic acid containing a vinyl group as described, for example, in WO 2000/031148 (incorporated herein by reference in its entirety) or from monomers that form [2+2] photo-cycloaddition reactions, for example, as described in WO 2001/001143 or WO 2003/0014392 (each of which is incorporated herein by reference in its entirety). Other suitable polymers are co-polymers of SFA and SFA derivatized with a bromo-acetamide group (e.g., BRAPA), or co-polymers of SFA and SFA derivatized with an azido-acetamide group.

The functionalized molecule (e.g., PAZAM) may be deposited on the surface of the silanized patterned wafer 10S (i.e., onto the silanized depressions and the silanized interstitial regions) using spin coating, or dipping or dip coating, or flow of the functionalized molecule under positive or negative pressure, or techniques set forth in U.S. Pat. No. 9,012,022, which is incorporated herein by reference in its entirety. The functionalized molecule may be present in a solution. In an example, the solution includes PAZAM in an ethanol and water mixture.

Figure 2C:
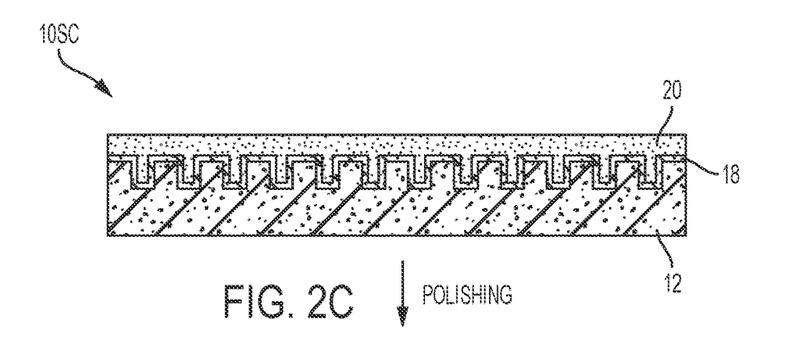

After being coated, the functionalized molecule may also be exposed to a curing process to form the coating layer 20 shown in FIG. 2C. In an example, curing the functionalized molecule may take place at a temperature ranging from room temperature (e.g., about 25° C.) to about 60° C. for a time ranging from about 5 minutes to about 2 hours.

The attachment of the functionalized molecule to the silanized depressions and silanized interstitial regions may be through covalent bonding. The covalent linking of the functionalized molecule to the silanized depressions is helpful for maintaining the coating layer 20 in the depressions 14, 14' throughout the lifetime of the ultimately formed flow cell during a variety of uses. The following are some examples of reactions that can take place between the silane or silane derivative 18 and the functionalized molecule.

When the silane or silane derivative 18 includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative 18 includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative 18 includes a bicyclononyne as the unsaturated moiety, the bicyclononyne can undergo similar SPAAC alkyne cycloaddition with azides or nitrile oxides attached to PAZAM due to the strain in the bicyclic ring system.

While not shown, it is to be understood that in some examples of the method, the patterned wafer 12 may not be exposed to silanization. Rather, the patterned wafer 12 may be exposed to plasma ashing, and then the functionalized molecule may be directly spin coated (or otherwise deposited) on the plasma ashed patterned wafer 12. In this example, plasma ashing may generate surface-activating agent(s) (e.g., —OH groups) that can adhere the functionalized molecule to the patterned wafer 12. In these examples, the functionalized molecule is selected so that it reacts with the surface groups generated by plasma ashing. In these examples, the surface-modified patterned wafer is formed by plasma ashing a surface of a patterned wafer 12 including depressions 14 separated by interstitial regions 16, forming the coating layer 20 of the functionalized molecule in the depressions 14 and on the interstitial regions 16, polishing the coating layer 20 from the interstitial regions 16 (optionally using i) a basic, aqueous slurry having a pH ranging from about 7.5 to about 11 and including an abrasive particle having a hardness that is less than a hardness of the patterned wafer or ii) a polishing pad and a solution free of the abrasive particle), and grafting a primer 22 to the coating layer 20 in the depressions 14 to form functionalized depressions. In some aspects, polishing is accomplished using an aqueous slurry comprising an abrasive particle with a hardness that is less than the hardness of the patterned wafer.

Referring back to the method shown in FIGS. 2A-2E, while not shown, it is to be understood that the silanized and coated patterned wafer 10SC (shown in FIG. 2C) may be exposed to a cleaning process. This process may utilize a water bath and sonication. The water bath may be maintained at a relatively low temperature ranging from about 22° C. to about 45° C. In another example the water bath temperature ranges from about 25° C. to about 30° C.

Figure 2D:
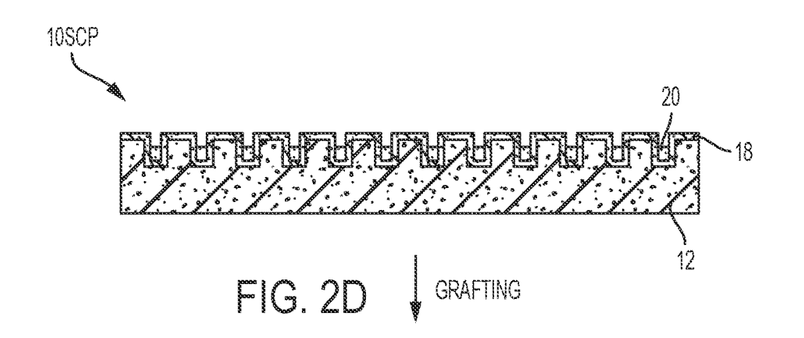

As shown between FIGS. 2C and 2D, the silanized and coated patterned wafer 10SC is then exposed to polishing to remove portion(s) of the coating layer 20 from the silanized interstitial regions. The polishing process disclosed herein is unlike typical polishing processes that are used in microelectromechanical system (MEMS) processing, which can involve harsh chemicals and hard, thick surfaces (e.g., metal). The silanized and coated patterned wafer 10SC is relatively soft, and the coating layer 20 may be about 200 nm or less in thickness. Given these conditions, a gentle chemical slurry (including an abrasive of a particular hardness and particle size) may be utilized during polishing, which can remove the thin coating layer 20 from the silanized interstitial regions without deleteriously affecting the underlying substrate 12 at those regions. Alternatively, a polishing may be performed with a solution that does not include the abrasive particles.

The gentle chemical slurry is a basic, aqueous slurry having a pH ranging from about 7.5 to about 11 and including an abrasive particle having a hardness that is less than a hardness of the patterned wafer 12 (which may have a hardness that is more than that of the coating layer 20). It is to be understood that the gentle chemical slurry may have any basic pH, for example, ranging from greater than 7 to 8 or from 11 to 14. In an example, the hardness of the patterned wafer 12 ranges from about 5 GPa to about 6 GPa, the hardness of the coating layer 20 ranges from about 0.5 GPa to about 0.7 GPa, and the hardness of the abrasive particle is about 0.2 GPa. However, it is to be understood that any abrasive particle that has a hardness less than the hardness of the patterned wafer 12 may be used. The hardness of the abrasive particles is selected so that the coating layer 20 in the depressions 14 is intact and at least substantially defect free after polishing is performed. Examples of the abrasive particle include calcium carbonate ($CaCO_3$), agarose, graphite, poly(methyl methacrylate) (PMMA), silica, aluminum oxide (i.e., alumina), ceria, polystyrene, and combinations thereof. In some examples, the abrasive particle is selected from the group consisting of calcium carbonate ($CaCO_3$), agarose, and graphite. The average particle size of the abrasive particles may range from about 15 nm to about 5 µm, and in one example is about 700 nm.

In addition to the abrasive particles, the basic, aqueous slurry may also include a buffer, a chelating agent, a surfactant, and/or a dispersant. An example of the buffer includes tris base (i.e., tris(hydroxymethyl)aminomethane), which may be present in a solution having a pH of about 9. An example of the chelating agent is ethylenediaminetetraacetic acid (EDTA), which may be present in a solution having a pH of about 8. An example of the surfactant is an anionic surfactant, such as sodium dodecyl sulfate. Polyacrylate dispersants having different molecular weights may be used. An example of the dispersant is poly(acrylic acid sodium salt). The dispersant may help to maintain the size of, and at least substantially prevent settling of the abrasive particles.

In an example, the basic, aqueous slurry is formed by adding the buffer to deionized (DI) water so the final molarity of the buffer is about 100 mM. In one example to achieve this molarity, the ratio of buffer to DI water is about 5:4. The chelating agent may be added in an amount of about 1 vol % (based on the total volume of the solution). In an example, the concentration of the chelating agent in the basic, aqueous slurry is about 1 mM. The dispersant may be added in an amount ranging from about 0.025 vol % to about 2.5 vol % (based on the total volume of the solution). This range for the dispersant contains a suitable value of zeta potential. The surfactant may be added in any suitable amount, an example of which includes about 0.125 vol %. The contents may be mixed, and then added to dry abrasive particle powder or beads to form a slurry. This slurry may be further diluted with DI water for polishing.

The basic, aqueous slurry may be used in a chemical mechanical polishing system to polish the surface of the silanized and coated patterned wafer 10SC. The polishing head(s)/pad(s) or other polishing tool(s) used in the system is/are capable of polishing the coating layer 20 from the interstitial regions 16 while leaving the coating layer 20 in the depressions 14, 14' and leaving the underlying substrate 12 at least substantially intact. As an example, the polishing head may be a Strasbaugh ViPRR II polishing head.

As mentioned above, polishing may be performed with a polishing pad and a solution without any abrasive. For example, the polish pad may be utilized with a solution free of the abrasive particle (i.e., a solution that does not include abrasive particles).

Polishing removes portion(s) of the coating layer 20 from the silanized interstitial regions and leaves portion(s) of the coating layer 20 in the silanized depressions, as shown in FIG. 2D. Also as shown in FIG. 2D, the interstitial region(s) 16 may remain silanized after polishing is complete. In other words, the silanized interstitial regions may remain intact after the polishing. Alternatively, the silane or silane derivative 18 may be removed from the interstitial region(s) 16 as a result of polishing.

While not shown, it is to be understood that the silanized, coated, and polished patterned wafer 10SCP (shown in FIG. 2D) may be exposed to a cleaning process. This process may utilize a water bath and sonication. The water bath may be maintained at a relatively low temperature ranging from about 22° C. to about 30° C. The silanized, coated, and polished patterned wafer 10SCP may also be spin dried, or dried via another suitable technique.

The silanized, coated, and polished patterned wafer 10SCP may then exposed to a process that will graft a primer 22 to the functionalized molecule coating layer 20 in the silanized depressions. Grafting of the primer(s) 22 forms functionalized depressions 15, an example of which is shown in the enlarged portion of FIG. 2E.

Examples of suitable primers 22 include forward amplification primers or reverse amplification primers. Specific examples of suitable primers 22 include P5 or P7 primers, which are used on the surface of commercial flow cells sold by Illumina Inc. for sequencing on HiSeq®, HiSeqX®, MiSeq®, MiSeqX®, NextSeq® and Genome Analyzer® instrument platforms.

Grafting may be accomplished by dunk coating, spray coating, puddle dispensing, slot die coating, or by another suitable method that will attach the primer(s) 22 to the coating layer 20 in at least some of the depressions 14, 14'. Each of these examples may utilize a primer solution or mixture, which may include the primer(s) 22, water, a buffer, and a catalyst.

Dunk coating may involve submerging the silanized, coated, and polished patterned wafer 10SCP into a series of temperature controlled baths. The baths may also be flow controlled and/or covered with a nitrogen blanket. The baths may include the primer solution or mixture. Throughout the various baths, the primer(s) 22 will attach to the coating layer 20 in at least some of the depression(s) 14, 14'. In an example, the silanized, coated, and polished patterned wafer 10SCP will be introduced into a first bath including the primer solution or mixture where a reaction takes place to attach the primer(s) 22, and then the array 10' will be moved to additional baths for washing. The silanized, coated, and polished patterned wafer 10SCP may be moved from bath to bath with a robotic arm or manually. A drying system, such as a heated nitrogen air-knife or spin coater, may also be used in dunk coating.

Spray coating may be accomplished by spraying the primer solution or mixture directly onto the silanized, coated, and polished patterned wafer 10SCP. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the silanized, coated, and polished patterned wafer 10SCP. The applied primer solution or mixture may be applied to or spread across the entire surface of the silanized, coated, and polished patterned wafer 10SCP. The primer coated wafer 10SCP may be incubated for a time ranging from about 2 minutes to about 60 minutes at a temperature ranging from about 0° C. to about 80° C. After incubation, the primer solution or mixture may be diluted and removed using, for example, the spin coater.

Figure 2E:
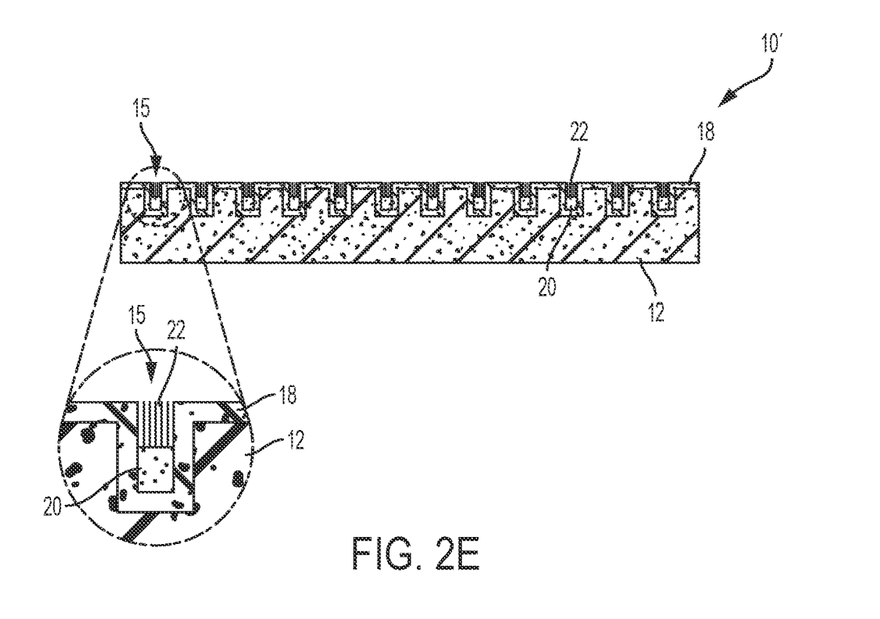

Grafting the primer(s) to the coating layer 20 in at least some of the silanized depression(s) 14, 14', forms functionalized depressions 15 as shown in FIG. 2E. After grafting, the desired surface chemistry has been applied, and the surface-modified patterned wafer 10' is formed.

The surface-modified patterned wafer 10' may be exposed to any desired quality control and/or surface characterization technique. For example, the surface-modified patterned wafer 10' may be exposed to, for example, atomic force microscopy (AFM), scanning electron microscopy (SEM), ellipsometry, goniometry, scatterometry, hybridization quality control methods, and/or fluorescence techniques.

Figure 3A:
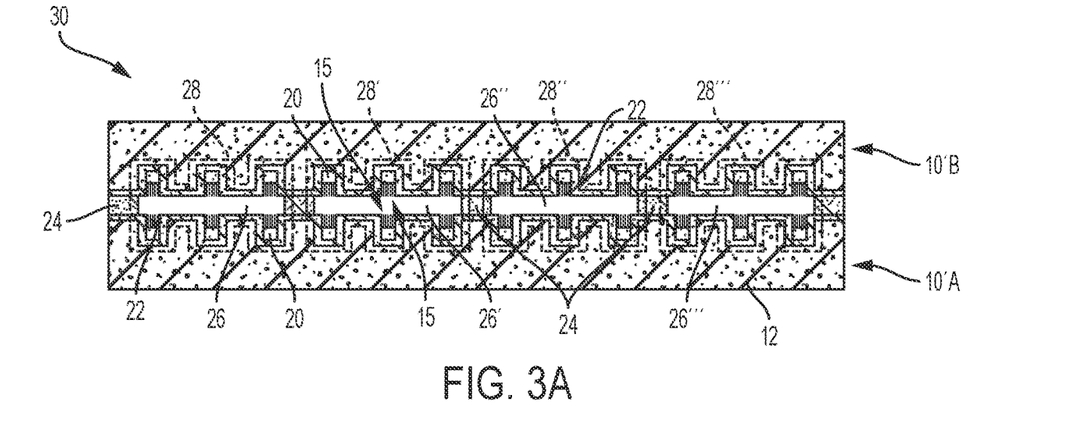
FIG. 3A is a cross-sectional view of an example flow cell package including two of the surface-modified patterned wafers bonded together, where the spacer layer defines fluidic chambers and the depressions are wells within a flow channel of a respective fluidic chamber.

The surface-modified patterned wafers 10' may be used to form a flow cell package 30, as shown in FIG. 3A. To form the flow cell package 30, two of the surface-modified patterned wafers 10' (shown as 10'A and 10'B in FIG. 3A) may be bonded together.

Generally, two surface-modified patterned wafers 10' may be positioned so that at least some of the functionalized depressions 15 of one (a first) of the surface-modified patterned wafers 10'A are aligned with at least some of the functionalized depressions 15 of the other (a second) of the surface-modified patterned wafers 10'B, and so that at least some of the interstitial regions 16 of one (the first) of the surface-modified patterned wafers 10'A are aligned with at least some of the interstitial regions 16 of the other (a second) of the surface-modified patterned wafers 10'B. The two surface-modified patterned wafers 10'A, 10'B may be bonded together at the at least substantially aligned interstitial regions 16. The two surface-modified patterned wafers may be bonded together at some of the at least substantially aligned interstitial regions, so as to define a plurality of discrete fluidic chambers. The two surface-modified patterned wafers may be bonded together in regions that do not comprise depressions. The two surface-modified patterned wafers may be bonded together at some of the at least substantially aligned interstitial regions and in regions of the wafers that lack depressions and are not interstitial regions (e.g., around the edges of the wafer). The wafer bonding may be accomplished using any suitable technique, such as laser bonding, diffusion bonding, anodic bonding, eutectic bonding, plasma activation bonding, glass frit bonding, or others methods known in the art.

Figure 3B:
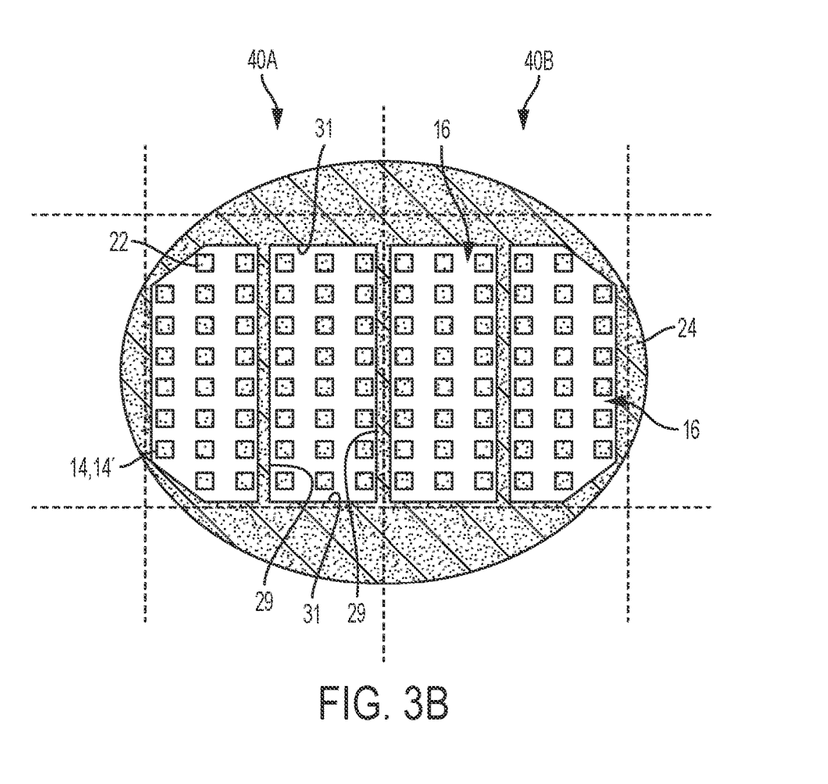
FIG. 3B is a top view of the flow cell package of FIG. 3A with the top surface-modified patterned wafer removed to more clearly show the spacer layer bonded to the bottom surface-modified patterned wafer, the dashed lines in FIG. 3B depict lines where the package may be diced to form individual flow cells.

The example shown in FIGS. 3A and 3B (the latter of which is top view of the package 30 without the upper surface-modified patterned wafers 10'B) includes a spacer layer 24 that is positioned in contact with, and bonds at least some of the at least substantially aligned interstitial regions 16. As shown from the top view in FIG. 3B, the spacer layer 24 may not contact all of the interstitial regions 16 of the wafers 10'A, 10'B. This may be desirable, for example, when several rows and columns of the functionalized depressions 15 are to be present in a single fluidic chamber 28, 28', 28", 28'. For example, the fluidic chambers 28, 28', 28", 28' of FIGS. 3A and 3B include three columns and eight rows of functionalized depressions 15, and the interstitial regions 16 within the fluidic chambers 28, 28', 28", 28''' remain exposed. It is to be understood that the spacer layer 24 may be precut to match the wafer size as well as the desirable number of fluidic chambers 28, 28', 28", 28''' that is to be formed.

In the example shown in FIGS. 3A and 3B, the fluidic chambers 28, 28', 28", 28''' are defined at least partially by the spacer layer 24 and are located between the two bonded surface-modified patterned wafers 10'A, 10'B. In the example shown in FIGS. 3A and 3B, the spacer layer 24 defines longitudinal walls 29 and ends 31 (FIG. 3B) of each of the fluidic chambers 28, 28' 28", 28'".

In this example, each fluidic chamber 28, 28', 28", 28'" includes a flow channel 26, 26', 26", 26'". Also in this example, each flow channel 26, 26', 26", 26'" is an area defined between the bonded surface-modified patterned wafers 10'A, 10'B that has the plurality of functionalized depressions 15 therein.

The spacer layer 24 may be any material that will seal at least some of the interstitial regions 16 of the surface-modified patterned wafers 10'A, 10'B together. Examples of the spacer layer 24 and bonding with the spacer layer 24 are described in U.S. Patent Publication No. 2016/0023208, which is incorporated herein by reference in its entirety.

In one example, the spacer layer 24 may be a radiation-absorbing material that absorbs radiation at a wavelength that is transmitted by the substrates 12. The absorbed energy, in turn, forms the bond between the spacer layer 24 and the respective surface-modified patterned wafers 10'A, 10'B. An example of this radiation-absorbing material is black Kapton® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm.

When the spacer layer 24 is the radiation-absorbing material, the spacer layer 24 may be positioned at an interface between the wafer 10'A and 10'B so that the spacer layer 24 contacts the desired silanized interstitial regions. Compression may be applied (e.g., approximately 50, 60, 70, 80, 90, or 100 PSI, or approximately 60 PSI of pressure) while laser energy at a suitable wavelength is applied to the interface (i.e., the radiation-absorbing material is irradiated). The laser energy may be applied to the interface both from the top and from the bottom in order to achieve suitable bonding between the spacer layer 24 and the respective wafers 10'A, 10'B.

In another example, the spacer layer 24 may include a radiation-absorbing material in contact therewith. The radiation-absorbing material may be applied at the interface between the spacer layer 24 and the wafers 10'A as well as at the interface between the spacer layer 24 and the wafers 10'B. As an example, the spacer layer 24 may be polyimide and the separate radiation-absorbing material may be carbon black. In this example, the separate radiation-absorbing material absorbs the laser energy that forms the bonds between the spacer layer 24 and the respective surface-modified patterned wafers 10'A, 10'B.

When the spacer layer 24 is in contact with a separate radiation-absorbing material, the radiation-absorbing material may be positioned at respective interfaces between the spacer layer 24 and each of the wafer 10'A and 10'B so that the radiation-absorbing material contacts at least some of the silanized interstitial regions of each of the wafers 10'A, 10'B as well as the spacer layer 24. Compression may be applied at the respective interfaces while laser energy at a suitable wavelength is applied to the interfaces (i.e., the radiation-absorbing material is irradiated). The laser energy may be applied to the interface both from the top and from the bottom in order to achieve suitable bonding between the spacer layer 24 and the respective wafers 10'A, 10'B.

In the example shown in FIGS. 3A and 3B, the spacer layer 24 (and bonding regions) may be located between the fluidic chambers 28 so that the spacer layer 24 physically separates one fluidic chamber 28 from an adjacent fluidic chamber 28 (to prevent cross-contamination) and may be located at the periphery of the wafers 10'A, 10'B (to seal the flow cell package 30). It is to be understood, however, that the spacer layer 24 (and bonding regions) may be located in any desired region depending on the implementation.

FIG. 3B also illustrates dashed lines where the flow cell package 30 can be diced to form respective flow cells 40A and 40B. The flow cell package 30 could be diced according to any desirable configuration, so that the individual flow cells 40A, 40B that are formed have at least two fluidic chambers 28. In some examples, it may be desirable to dice the packaged flow cell 30 so that each flow cell 40A, 40B includes eight separate fluidic chambers. In other examples, the flow cell package is diced to form two, three, four, or more flow cells. In other examples, each flow cell includes one, two, three, four, five, six, seven, or eight separate fluidic chambers. In other example, each flow cell includes two, four, or eight separate fluidic chambers.

Figure 4A:
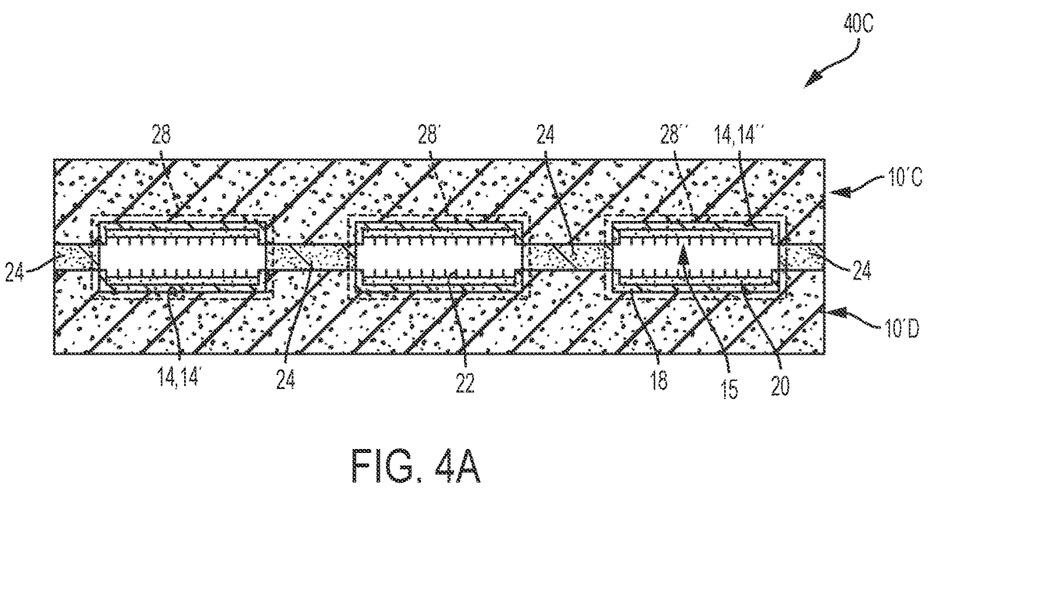
FIG. 4A is a cross-sectional view of an example flow cell package including two of the surface-modified patterned wafers bonded together, where the spacer layer defines fluidic chambers and the depressions are flow channels that are respective associated with one fluidic chamber.
Figure 4B:
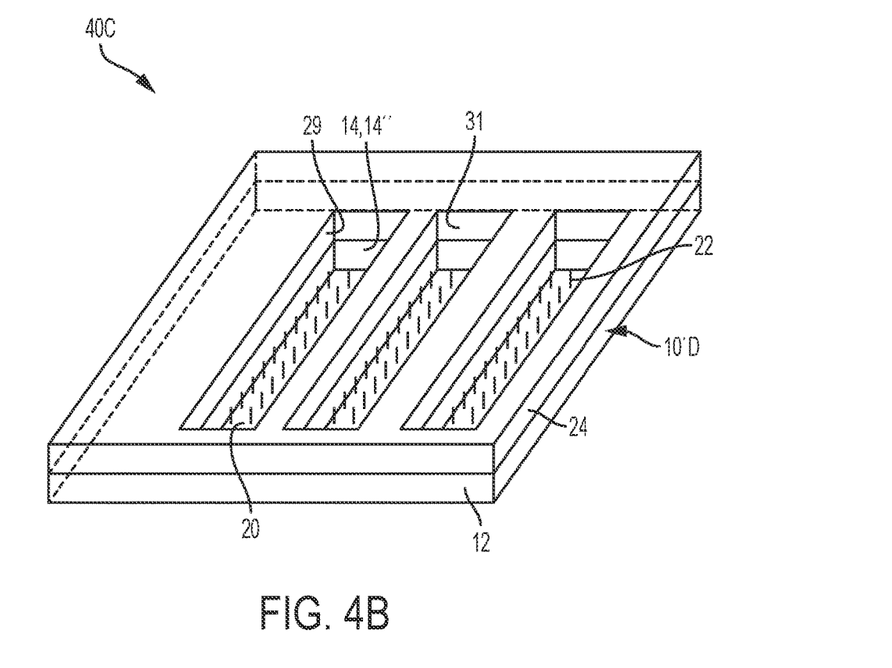
FIG. 4B is a perspective view of the flow cell package of FIG. 4A with the top surface-modified patterned wafer removed to more clearly show the flow channels.

Referring now to FIGS. 4A and 4B, another example of a flow cell 40C is depicted. It is to be understood that this flow cell 40C may be formed as part of a flow cell package in accordance with the method(s) disclosed herein. As such, the flow cell 40C is shown after the flow cell package has been diced. In this example, the respective depressions 14 (and thus functionalized depressions 15) are flow channels 14" that extend across a substantial portion of the length of the substrate 12 of each wafer portion 10'C, 10'D (rather than the wells 14' shown in the previous figures).

The flow cell 40C includes two surface-modified patterned wafer portions 10'C, 10'D that are bonded together with the spacer layer 24 at the bonding regions. In this example, the spacer layer 24 may contact all of the interstitial regions 16 of the wafer portions 10'C, 10'D. This may be desirable, for example, when the functionalized depressions 15 are elongated fluidic channels 14" rather than discrete wells 14'. Each channel 14" is associated with a single fluidic chamber 28, 28', 28".

In the example shown in FIGS. 4A and 4B, the fluidic chambers 28, 28', 28" are defined, in part, by the spacer layer 24 and are located between the two bonded surface-modified patterned wafer portions 10'C, 10'D. In the example shown in FIGS. 4A and 4B, the spacer layer 24 defines part of the longitudinal walls 29 and ends 31 of each of the fluidic chambers 28, 28', 28", while the depressions/flow channels 14' 14" of each wafer portion 10'C, 10'D form the remainder of the longitudinal walls 29 and ends 31 of each of the fluidic chambers 28, 28', 28".

The flow cells 40A, 40B, 40C may be used to perform controlled chemical or biochemical reactions in a reaction automation device, such as in a nucleotide sequencer. While not shown, it is to be understood that ports may be drilled through the substrate 12 of the bottom surface-modified patterned wafers 10'A, 10'D to respective fluidic chambers 28. By connecting to ports, the reaction automation device may control the flow of reagent(s) and product(s) in the sealed fluidic chambers 28. The reaction automation device may, in some applications, adjust the pressure, temperature, gas composition and other environmental conditions of the flow cell 40A, 40B, 40C. Further, in some applications, ports may be drilled in the substrate 12 of the top surface-modified patterned wafers 10'B, 10'C or in both the top and bottom substrates 12. In some applications, the reactions taking place in sealed fluidic chambers 28 may be monitored through the substrate(s) 12 by imaging or measurements of heat, light emission and/or fluorescence.

The flow cells 40A, 40B, 40C disclosed herein may be used in a variety of sequencing approaches or technologies, including techniques often referred to as sequencing-by-synthesis (SBS), sequencing-by-ligation, pyrosequencing, and so forth. With any of these techniques, since the functionalized molecule and attached sequencing primer(s) 22 are present in the functionalized depressions and not on the interstitial regions 16, amplification will be confined to the functionalized depressions.

Briefly, a sequencing by synthesis (SBS) reaction may be run on a system such as the HiSeq®, HiSeqX®, MiSeq® or NextSeq® sequencer systems from Illumina (San Diego, CA). A set of target DNA molecules to be sequenced is hybridized to the bound sequencing primers 22 and then amplified by bridge amplification or by kinetic exclusion amplification. Denaturation leaves single-stranded templates anchored to the functionalized molecule (coating layer 20), and several million dense clusters of double-stranded DNA are generated (i.e., cluster generation). The sequencing reactions are then carried out. The data are aligned and compared to a reference, and sequencing differences are identified.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All publications, patents, and patent applications cited in this Specification are hereby incorporated by reference in their entirety.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 200 mm to about 300 mm, should be interpreted to include not only the explicitly recited limits of from about 200 mm to about 300 mm, but also to include individual values, such as about 208 mm, about 245 mm, about 275.5 mm, etc., and sub-ranges, such as from about 225 mm to about 990 mm, from about 235 mm to about 280 mm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A flow cell package, comprising:
   a first surface-modified patterned wafer, consisting of:
     first depressions separated by first interstitial regions;
     a first functionalized molecule bound to a first silane or a first silane derivative in at least some of the first depressions; and
     a first primer grafted to the first functionalized molecule in the at least some of the first depressions;
   a second surface-modified patterned wafer, consisting of:
     second depressions separated by second interstitial regions;
     a second functionalized molecule bound to a second silane or a second silane derivative in at least some of the second depressions; and
     a second primer grafted to the second functionalized molecule in the at least some of the second depressions; and
   a spacer layer bonding at least some of the first interstitial regions to at least some of the second interstitial regions, wherein the spacer layer at least partially defines respective fluidic chambers of the flow cell package.

2. The flow cell package as defined in claim 1, wherein:
   each one of the respective fluidic chambers includes at least one aligned functionalized depression pair, wherein the at least one aligned functionalized depression pair includes one of the first depressions aligned with one of the second depressions; and
   the spacer layer forms longitudinal walls between adjacent fluidic chambers.

3. The flow cell package as defined in claim 1, wherein at least one of the first and second depressions is:
   in a flow channel defined by the two bound surface-modified patterned wafers; or
   one of a plurality of wells within the flow channel.

4. The flow cell package as defined in claim 1, wherein:
   each of the first functionalized molecule and the second functionalized molecule includes a recurring unit of Formula (I):

wherein:
   $R^1$ is H or optionally substituted alkyl;
   $R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
   $R^5$ is selected from the group consisting of H and optionally substituted alkyl;
   each of the —$(CH_2)_p$— can be optionally substituted;
   p is an integer in the range of 1 to 50;

n is an integer in the range of 1 to 50,000; and
m is an integer in the range of 1 to 100,000.

5. The flow cell package as defined in claim 1, wherein:
the first functionalized molecule is covalently bound to the first silane or the first silane derivative through a first unsaturated moiety of the first silane or first silane derivative;
the second functionalized molecule is covalently bound to the second silane or the second silane derivative through a second unsaturated moiety of the second silane or second silane derivative; and
the unsaturated moieties are individually selected from the group consisting of norbornene, heteronorbornenes, norbornene derivatives, transcyclooctene, transcyclooctene derivatives, cyclooctyne, bicycloalkynes, optionally substituted variants thereof, and combinations thereof.

6. The flow cell package as defined in claim 1, wherein the spacer layer comprises a black polyimide.

7. The flow cell package as defined in claim 1, wherein each of the first surface-modified patterned wafer and the second surface-modified patterned wafer has a diameter ranging from about 200 mm to about 300 mm.

8. The flow cell package as defined in claim 1, comprising a plurality of flow cells.

9. A flow cell package, comprising:
first and second surface-modified patterned wafers and a spacer layer,
wherein the first surface-modified patterned wafer consists of first depressions separated by first interstitial regions, a first functionalized molecule bound to the first surface-modified patterned wafer in at least some of the first depressions, and a first primer grafted to the first functionalized molecule in the at least some of the first depressions;
the second surface-modified patterned wafer consists of second depressions separated by second interstitial regions, a second functionalized molecule bound to the second surface-modified patterned wafer in at least some of the second depressions, and a second primer grafted to the second functionalized molecule in the at least some of the second depressions; and
the spacer layer bonds at least some first interstitial regions to at least some second interstitial regions, and the spacer layer at least partially defines respective fluidic chambers of the flow cell package.

10. The flow cell package as defined in claim 9, wherein: each one of the respective fluidic chambers includes at least one aligned functionalized depression pair, wherein the at least one aligned functionalized depression pair includes one of the first depressions aligned with one of the second depressions; and
the spacer layer forms longitudinal walls between adjacent fluidic chambers.

11. The flow cell package as defined in claim 9, wherein at least one of the first and second depressions is:
in a flow channel defined by the two bound surface-modified patterned wafers; or
one of a plurality of wells within the flow channel.

12. The flow cell package as defined in claim 9, wherein:
each of the first functionalized molecule and the second functionalized molecule includes a recurring unit of Formula (I):

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the $-(CH_2)_p-$ can be optionally substituted;
p is an integer in the range of 1 to 50;
n is an integer in the range of 1 to 50,000; and
m is an integer in the range of 1 to 100,000.

13. The flow cell package as defined in claim 9, wherein the spacer layer comprises a black polyimide.

14. The flow cell package as defined in claim 9, wherein each of the first surface-modified patterned wafer and the second surface-modified patterned wafer has a diameter ranging from about 200 mm to about 300 mm.

15. The flow cell package as defined in claim 9, comprising a plurality of flow cells.

* * * * *